(12) United States Patent
Hatakeyama et al.

(10) Patent No.: US 7,456,311 B2
(45) Date of Patent: *Nov. 25, 2008

(54) ADAMANTANE DERIVATIVE, PROCESS FOR PRODUCING THE SAME, AND PHOTOSENSITIVE MATERIAL FOR PHOTORESIST

(75) Inventors: Naoyoshi Hatakeyama, Chiba (JP); Shinji Tanaka, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/575,555

(22) PCT Filed: Sep. 21, 2005

(86) PCT No.: PCT/JP2005/017400

§ 371 (c)(1),
(2), (4) Date: Mar. 19, 2007

(87) PCT Pub. No.: WO2006/033359

PCT Pub. Date: Mar. 30, 2006

(65) Prior Publication Data

US 2008/0009647 A1 Jan. 10, 2008

(30) Foreign Application Priority Data

Sep. 24, 2004 (JP) .............................. 2004-277184

(51) Int. Cl.
*C07C 69/52* (2006.01)
(52) U.S. Cl. ....................... 560/220; 560/222
(58) Field of Classification Search ........................ None
See application file for complete search history.

(56) References Cited

U.S. PATENT DOCUMENTS

2002/0058197 A1* 5/2002 Nozaki et al. ............ 430/270.1

2007/0129532 A1* 6/2007 Hatakeyama et al. ....... 528/326

FOREIGN PATENT DOCUMENTS

| EP | 2005/075406 | 8/2005 |
|---|---|---|
| JP | 2001 48933 | 2/2001 |
| JP | 2001 097928 | 4/2001 |
| JP | 2001 343748 | 12/2001 |
| JP | 2002 148805 | 5/2002 |
| JP | 2004 069981 | 3/2004 |
| JP | 2005-220066 | 8/2005 |

OTHER PUBLICATIONS

<http://www.organic-chemistry.org/namedreactions/nucleophilic-substitution-sn1-sn2.shtm>[visited Dec. 3, 2007].*
U.S. Appl. No. 11/575,555, filed Mar. 19, 2007, Hatakeyama, et al.
U.S. Appl. No. 10/588,080, filed Jan. 10, 2007, Hatakeyama, et al.

* cited by examiner

*Primary Examiner*—Karl J Puttlitz
(74) *Attorney, Agent, or Firm*—Oblon, Spivak, McClelland, Maier & Neustadt, P.C.

(57) ABSTRACT

The invention provides a novel adamantane derivative useful as a monomer for producing functional resins such as photosensitive resins particularly for use in lithography, and a method for producing the derivative. The adamantane derivative has a structure represented by formula (I-a) and the method for producing the adamantane derivative employs a corresponding adamantane derivative serving as a starting material. In formula (I), $R^1$ represents H, $CH_3$, or $CF_3$; $R^{2a}$ represents a C1 to C30 alkyl group or a hydrocarbon group containing a C3 to C30 cycloalkyl group or a C6 to C30 aryl group, the alkyl group or the hydrocarbon group having a hetero atom; each of $X^1$ and $X^2$ represents O or S; Y represents a C1 to C10 alkyl group, a halogen atom, OH, or SH, or two Ys are linked to form =O or =S; k represents an integer of 0 to 14; and each of m and n is an integer of 0 to 2.

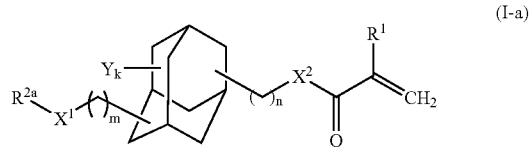

(I-a)

6 Claims, No Drawings

ADAMANTANE DERIVATIVE, PROCESS FOR PRODUCING THE SAME, AND PHOTOSENSITIVE MATERIAL FOR PHOTORESIST

TECHNICAL FIELD

The present invention relates to a novel adamantane derivative, to a method for producing the derivative, and to a photosensitive material for photoresists produced from the adamantane derivative. More particularly the invention relates to a novel modified alkyl (thio)ether-substituted adamantyl (meth)acrylate useful as a monomer for producing functional resins such as photosensitive resins particularly for use in lithography, to an effective method for producing the derivative, and to a photosensitive material for photoresists containing a polymer produced from the modified alkyl (thio)ether-substituted adamantyl (meth)acrylate.

BACKGROUND ART

Adamantane is a stable compound having a highly symmetric structure in which four cyclohexane rings are condensed to form a cage. Derivatives of adamantane are known to exhibit a variety of functions, and thus the derivatives are useful sources for drugs high-function industrial materials, etc. For example, Patent Document 1 and 2 etc. disclose studies on use of such derivatives as optical disk substrates, optical fibers, lenses, etc. by virtue of their useful properties such as optical characteristics and heat resistance.

Patent Document 3 discloses studies on use of adamantane esters as a source resin for photoresists on the basis of properties thereof such as acid-sensitivity, dry-etching resistance, and UV transmittance.

In a trend of recent years toward micro-scaling of semiconductor devices, a lithographic step in the production of semiconductor devices is required to be performed with more rigorous micro-scale precision. To satisfy the requirement, there have been studied various micro-pattern formation methods employing a photoresist which functions with respect to a short-wavelength radiation such as a KrF beam an ArF beam, or an $F_2$ excimer laser beam These patterning formation methods employing such exposure techniques have now been developed to liquid-immersion lithography. The new lithographic technique has a drawback in that the range of depth of focus (DOF) where resolution of the photocured resin is ensured becomes considerably narrower with an increase in the numerical aperture (NA) of the lens employed in photolithography. In order to overcome the drawbacks there is a demand for a new photoresist material which can improve DOF characteristics; i.e., a high-refractive-index resist material which ensures resolution within a wide DOF margin (an area ensuring resolution even when the area is apart from the focus), even when a high-NA exposure light is employed.

Meanwhile, a modified alkyl (thio)ether-substituted polymerizable adamantane derivative has never been developed, since synthesis of such a compound is technically difficult.

[Patent Document 1]
Japanese Patent Application Laid-Open (kokai) No. Heisei 6(1994)-305044
[Patent Document 2]
Japanese Patent Application Laid-Open (kokai) No. Heisei 9(1997)-302077
[Patent Document 3]
Japanese Patent Application Laid-Open (kokai) No. Heisei 4(1992)-39665

DISCLOSURE OF THE INVENTION

Problems to be Solved by the Invention

The present invention has been conceived under such circumstances, and an object of the present invention is to provide a novel adamantane derivative useful as a monomer for producing functional resins such as photosensitive resins for use in lithography. Another object of the invention is to provide a method for producing the derivative. Still another object of the invention is to provide a photosensitive material for photoresists produced from the adamantane derivative.

Means for Solving the Problems

The present inventors have conducted extensive studies in order to attain the aforementioned object, and have found that a modified alkyl (thio)ether-substituted adamantyl (meth) acrylate having a specific structure is a novel compound which meets the requirement, and that the compound can be produced at high efficiency from a compound having the corresponding adamantyl group. The present invention has been accomplished on the basis of these findings.

Accordingly, the present invention provides an adamantine derivatives and photosensitive material for photoresist, as described below.

1. An adamantane derivative having a structure represented by formula I-a):

[F1]

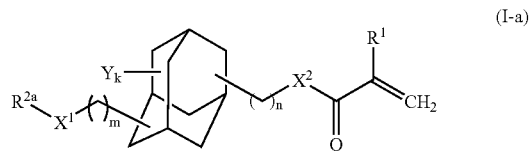

(I-a)

(wherein $R^1$ represents a hydrogen atom, a methyl group, or a trifluoromethyl group; $R^{2a}$ represents a C1 to r30 alkyl group or a hydrocarbon group containing a C3 to C30 cycloalkyl group or a C6 to C30 aryl group, the alkyl group or the hydrocarbon group having a hetero atom; each of $X^1$ and $X^2$ represents an oxygen atom or a sulfur atom; Y represents a C1 to C10 alkyl group, a halogen atom, a hydroxyl group, or a mercapto group, or two Ys are linked to form =O or =S; a plurality of Ys may be identical to or different from one another; k represents an integer of 0 to 14; and each of m and n is an integer of 0 to 2).

2. A method for producing an adamantane derivative having a structure represented by formula (I-a):

[F2]

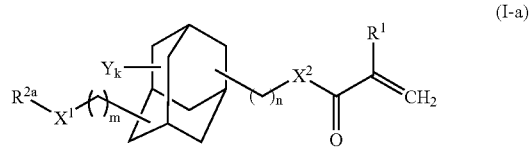

(I-a)

(wherein $R^1$, $R^{2a}$, $X^1$, $X^2$, Y, k, m, and n have the same meanings as defined above), wherein the method comprises employing, as a starting material, an adamantane derivative represented by formula (II):

[F3]

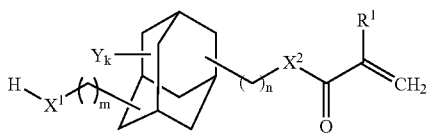

(II)

(wherein $R^1$, $X^1$, $X^2$, Y, k, m, and n have the same meanings as defined above).

3. A method as described in 2 above, wherein the adamantane derivative represented by formula (II) is 3-hydroxy-1-adamantyl (meth)acrylate.
4. A method for producing an adamantane derivative having a structure represented by formula (I-b):

[F4]

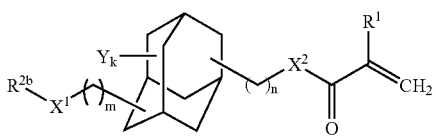

(I-b)

(wherein $R^1$, $X^1$, $X^2$, Y, k, m, and n have the same meanings as defined above; $R^{2b}$ represents a C1 to C30 alkyl group or a hydrocarbon group containing a C3 to C30 cycloalkyl group or a C6 to C30 aryl group; and $R^{2b}$ may have a hetero atom), wherein the method comprises employing, as a starting material, an adamantane derivative represented by formula (III):

[F5]

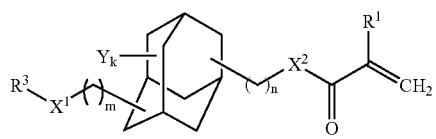

(III)

(wherein $R^1$, $X^1$, $X^2$, Y, k, m, and n have the same meanings as defined above, and $R^3X^1$ represents a leaving group).

5. A method as described in 4 above, wherein the adamantane derivative represented by formula (III) may be 3-methanesulfonyloxy-1-adamantyl (meth)acrylate.
6. In a fourth aspect of the present invention, there is provided a photosensitive material for photoresist, which material comprises a polymer formed from, as a component thereof, an adamantane derivative represented by formula (I-a):

[F6]

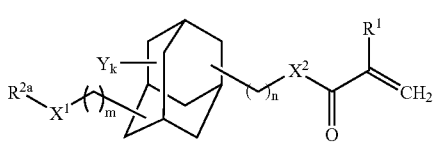

(I-a)

(wherein $R^1$, $R^{2a}$, $X^1$, $X^2$, Y, k, m, and n have the same meanings as defined above).

Effects of the Invention

The adamantane derivative according to the present invention is a novel modified alkyl (thio)ether-substituted adamantyl (meth)acrylate, which is useful as a monomer for producing functional resins such as photosensitive resins for use in lithography. The photosensitive material for photoresists containing a polymer of the adamantane derivative ensures resolution within a wide depth of focus (DOF) range even when exposure light of a large numerical aperture (NA) is employed. The photosensitive material is expected to attain high resolution.

BEST MODES FOR CARRYING OUT THE INVENTION

The adamantane derivative of the present invention is a compound represented by formula (I-a), which is an absolutely novel compound which has never been disclosed in the literature. Hereinafter, the compound and the production method will be described.

The adamantane derivative of the present invention is a modified alkyl (thio)ether-substituted adamantyl (meth)acrylate having a structure represented by the following formula (I-a).

[F7]

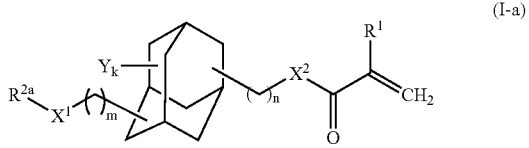

(I-a)

In formula (1-a), $R^1$ represents a hydrogen atom, a methyl group, or a trifluoromethyl group; $R^{2a}$ represents a C1 to C30 alkyl group or a hydrocarbon group containing a C3 to C30 cycloalkyl group or a C6 to C30 aryl group, the alkyl group or the hydrocarbon group having a hetero atom; each of $X^1$ and $X^2$ represents an oxygen atom or a sulfur atom; Y represents a C1 to C10 alkyl group, a halogen atom, a hydroxyl group, or a mercapto group, or two Ys are linked to form =O or =S; a plurality of Ys may be identical to or different from one another; k represents an integer of 0 to 14; and each of m and n is an integer of 0 to 2.

The C1 to C30 alkyl group denoted by $R^{2a}$ may be a linear or branched-chain alkyl group. Examples of the alkyl group include a methyl group, an ethyl group, various propyl groups, various butyl groups, various pentyl groups, various hexyl groups, various heptyl groups, various octyl groups, various nonyl groups, various decyl groups, various dodecyl groups, and various tetradecyl groups. Examples of the C3 to C-30 cycloalkyl group contained in the hydrocarbon group include a cyclopentyl group and a cyclohexyl group. Examples of the C6 to C30 aryl group contained in the hydrocarbon group include a phenyl group, a tolyl group, a xylyl group, a naphthyl group, and a methylnaphthyl group. Examples of the hetero atom include nitrogen, oxygen, and sulfur.

The C1 to C10 alkyl group denoted by Y may be linear, branched, or cyclic. Examples of the alkyl group include a methyl group, an ethyl group, various propyl groups, various butyl groups, various pentyl groups, various hexyl groups, various heptyl groups, various octyl groups, various nonyl groups, various decyl groups, a cyclopentyl group, and a cyclohexyl group. These alkyl groups may be substituted by an appropriate group such as a halogen atom or a hydroxyl group. The "n" is preferably 0. Examples of the halogen atom denoted by Y include fluorine, chlorine, bromine, and iodine.

Examples of the compound represented by formula (I) include 3-methylthiomethyloxy-1-adamantyl acrylate, 3-(methylthiomethyloxy)methyl-1-adamantylmethyl acrylate, 2-[3-[2-(methylthiomethyloxy)ethyl]-1-adamantyl] ethyl acrylate, 3-[(1-ethylthio)ethan-1-yloxy]-1-adamantyl acrylate, 3-[(1-ethylthio)ethan-1-yloxy]methyl-1-adamantylmethyl acrylate, 2-{3-[2-[(1-ethylthio)ethan-1-yloxy] ethyl]-1-adamantyl}ethyl acrylate, 3-[(1-propylthio)propan-1-yloxy]-1-adamantylmethyl acrylate, 3-[(1-propylthio) propan-1-yloxy]methyl-1-adamantylmethyl acrylate, 2-{3-[2-[(1-propylthio)propan-1-yloxy]ethyl]-1-adamantyl}ethyl acrylate, 3-[(1-butylthio)butan-1-yloxy]-1-adamantyl acrylate, 3-[(1-butylthio)butan-1-yloxy]methyl-1-adamantylmethyl acrylate, 2-{3-[2-[(1-butylthio)butan-1-yloxy]ethyl]-1-adamantyl}ethyl acrylate, 3-phenylthiomethyloxy-1-adamantyl acrylate, 3-(phenylthiomethyloxy)methyl-1-adamantylmethyl acrylate, 2-[3-[2-(phenylthiomethyloxy) ethyl]-1-adamantyl]ethyl acrylate, 3-methylthiomethylthio-1-adamantyl acrylate, 3-(methylthiomethylthio)methyl-1-adamantylmethyl acrylate, 2-[3-[2-(methylthiomethylthio) ethyl]-1-adamantyl]ethyl acrylate, 3-[(1-ethylthio)ethan-1-ylthio]-1-adamantyl acrylate, 3-[(1-ethylthio)ethan-1-ylthio] methyl-1-adamantylmethyl acrylate, 2-{3-[2-[(1-ethylthio) ethan-1-ylthio]ethyl]-1-adamantyl}ethyl acrylate, 3-[(1-propylthio)propan-1-ylthio]-1-adamantylmethyl acrylate, 3-[(1-propylthio)propan-1-ylthio]methyl-1-adamantylmethyl acrylate, 2-{3-[2-[1-propylthio)propan-1-ylthio]ethyl]-1-adamantyl}ethyl acrylate, 3-[1-butylthio)butan-1-ylthio]-1-adamantyl acrylate, 3-[(1-butylthio)butan-1-ylthio] methyl-1-adamantylmethyl acrylate, 2-{3-[2-[(1-butylthio) butan-1-ylthio]ethyl]-1-adamantyl}ethyl acrylate, 3-phenylthiomethylthio-1-adamantyl acrylate, 3-(phenylthiomethylthio)methyl-1-adamantylmethyl acrylate, 2-[3-[2-(phenylthiomethylthio)ethyl]-1-adamantyl]ethyl acrylate, 3-methylthiomethyloxy-1-adamantyl α-trifluoromethylacrylate, 3-(methylthiomethyloxy)methyl-1-adamantylmethyl α-trifluoromethylacrylate, 3-(methylthiomethyloxy) ethyl-1-adamantylethyl α-trifluoromethylacrylate, 3-methylthiomethylthio-1-adamantyl α-trifluoromethylacrylate, 3-(methylthiomethylthio)methyl-1-adamantylmethyl α-trifluoromethylacrylate, and 3-(methylthiomethylthio)ethyl-1-adamantylethyl α-trifluoromethylacrylate. Similar compounds, which are derived by substituting the acrylate group of these compounds with methacrylate, α-trifluoromethylacrylate, S-thioacrylate, S-thiomethacrylate, or S-thio-α-trifluoromethylacrylate, are also included in the compound represented by formula (I).

Of these, 3-methylthiomethyloxy-1-adamantyl acrylate and 3-methylthiomethyloxy-1-adamantyl methacrylate are preferred.

The adamantane derivative of the present invention represented by formula (I-a) may be synthesized from an adamantane derivative re-resented by the following formula (II):

[F8]

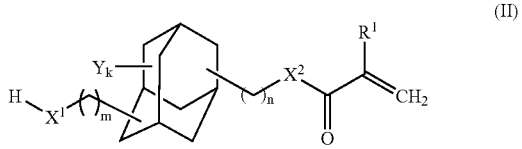

(wherein $R^1$, $X^1$, $X^2$, Y, k m, and n have the same meanings as defined above) serving as a starting material. Examples of the adamantane derivative represented by formula (II) include 3-hydroxy-1-adamantyl acrylate (Adamantate HA, product of Idemitsu Kosan Co., Ltd.), 3-hydroxy-1-adamantyl methacrylate (Adamantate HM, product of Idemitsu Kosan Co., Ltd.), 3-hydroxy-1-adamantyl α-trifluoromethylacrylate, [3-(hydroxymethyl)-1-adamantyl]methyl acrylate, [3-(hydroxymethyl)-1-adamantyl]methyl methacrylate, [3-(hydroxymethyl)-1-adamantyl]methyl α-trifluoromethylacrylate, [3-(hydroxyethyl)-1-adamantyl] ethyl acrylate, [3-(hydroxyethyl)-1-adamantyl]ethyl methacrylate, [3-(hydroxyethyl)-1-adamantyl]ethyl α-trifluoromethylacrylate, 2-[3-(2-hydroxyethyl)-1-adamantyl]ethyl acrylate, 2-[3-(2-hydroxyethyl)-1-adamantyl]ethyl methacrylate, 2-[3-(2-hydroxyethyl)-1-adamantyl]ethyl α-trifluoromethylacrylate, 3-mercapto-1-adamantyl acrylate, 3-mercapto-1-adamantyl methacrylate, 3-mercapto-1-adamantyl α-trifluoromethylacrylate, [3-(mercaptomethyl)-1-adamantyl]methyl acrylate, [3-(mercaptomethyl)-1-adamantyl]methyl methacrylate, [3-(mercaptomethyl)adamantyl]methyl α-trifluoromethylacrylate, [3-(mercaptoethyl)-1-adamantyl] ethyl acrylate, [3-(mercaptoethyl)-1-adamantyl]ethyl methacrylate, [3-(mercaptoethyl)adamantyl]ethyl α-trifluoromethylacrylate, 2-[3-(2-mercaptoethyl)-1-adamantyl]ethyl acrylate, 2-[3-(2-mercaptoethyl)-1-adamantyl]ethyl methacrylate, and 2-[3-(2-mercaptoethyl)-1-adamantyl]ethyl α-trifluoromethylacrylate. Similar compounds, which are derived by substituting the acrylate, methacrylate or α-trifluoromethylacrylate of these compounds with S-thioacrylate, S-thiomethacrylate or S-thio-α-trifluoromethylacrylate, respectively, are also included in the compound represented by formula (II). Of these, 3-hydroxy-1-adamantyl acrylate (Adamantate HA, product of Idemitsu Kosan Co., Ltd.) and 3-hydroxy-1-adamantyl methacrylate (Adamantate HM, product of Idemitsu Kosan Co., Ltd.) are preferred in the present invention.

The adamantane derivative represented by formula (I-a) may be produced from an adamantane derivative represented by formula II) serving as a starting material. In the case where the heteroatom in $R^{2a}$ is a sulfur atom, reaction, for example, between the adamantane derivative and sulfoxide in an acid anhydride forms the formula (I-a) adamantane derivative.

Examples of the sulfoxide include dimethyl sulfoxide, diethyl sulfoxide, di-n-propyl sulfoxide, diisopropyl sulfoxide, di-n-butyl sulfoxide, diisobutyl sulfoxide, di-sec-butyl sulfoxide, diisopentyl sulfoxide, didodecyl sulfoxide, phenyl methyl sulfoxide, phenyl ethyl sulfoxide, p-tolyl methyl sulfoxide, ethyl thiomethyl sulfoxide, ethyl naphthyl sulfoxide, ethyl p-tolyl sulfoxide, methyl phenyl sulfoxide, methyl p-tolyl sulfoxide, and phenyl propyl sulfoxide. In the present inventions dimethyl sulfoxide is preferred.

The sulfoxide is generally fed in an amount of about 1 to about 100 mol based on the 1 mol of the adamantane derivative represented by formula (II), preferably 20 to 40 mol.

Examples of the acid anhydride include acetic anhydride, propionic anhydride, butyric anhydride, isobutyric anhydride, valeric anhydride, pivalic anhydride, benzoic anhydride, chloroacetic anhydride, and trifluoroacetic anhydrlde. Of these, acetic anhydride is preferred in the present invention.

The acid anhydride is generally fed in an amount of about 1 to about 100 mol based on the 1 mol of the adamantane derivative represented by formula (II), preferably 10 to 30 mol.

In the above reaction, a solvent is employed in accordance with needs. In other words, when the adamantane derivative represented by formula (II) can be dissolved in a mixed solution of the sulfoxide and the acid anhydride, no particular solvent is needed. However, a solvent may be employed in accordance with needs.

The solvent employed in the invention preferably has a solubility (at reaction temperature) of the adamantane derivative represented by formula (II) of 0.5 mass % or more, more preferably 5 mass % or more. The amount of the solvent is such that the adamantane derivative concentration of the reaction mixture is preferably adjusted to 0.5 mass % or more, more preferably 5 mass % or more. In this case, the aforementioned derivative may be in the form of dispersion and is preferably in the form of solution. Preferably, water contained in the solvent is removed before use. Specific examples of the solvent include hydrocarbon solvents such as n-hexane and n-heptane; ether solvents such as diethyl ether and tetrahydrofuran (THF); and halogen-containing solvents such as dichloromethane and carbon tetrachloride. These solvents may be used singly or in combination or two or more species.

In the case where the heteroatom in $R^{2a}$ is a sulfur atom, the adamantane derivative represented by formula (I-a) may be synthesized through for example, the following procedure. An adamantane derivative represented by formula (II) is reacted with dialkyl sulfoxide in an acid anhydride. After completion of reaction, the reaction mixture is neutralized, and the formed salt is removed through washing with water. Subsequently the formed adamantyl-group-containing polymer and adamantyl-group-containing oligomer are removed through re-precipitation, to thereby synthesize the formula (I-a) adamantane derivative.

The reaction is generally performed at −200° C. to 200° C. However, in consideration of factors such as rate of reaction and prevention of by-production of polymer, the reaction temperature is preferably −50° C. to 50° C. When the reaction temperature is adjusted to −200° C. or higher, an appropriate rate of reaction is ensured. When the reaction temperature is adjusted to 200° C. or lowers the amount of by-produced polymer decreases. The pressure at which the reaction is performed is generally an absolute pressure of 0.01 to 10 MPa. When the pressure falls within the range, a particularly designed pressure-resistant apparatus is not needed, which is economically advantageous. The pressure is preferably normal pressure to 1 MPa. The reaction time is generally 1 to 120 hours, preferably 6 to 48 hours. When the reaction time is our hour or longer, practically effective percent conversion can be attained. When the reaction time is 120 hours or shorter, production efficiency increases. In other words, a reaction time of 1 to 120 hours is economically advantageous.

In one embodiment of the re-precipitation process, a solvent for re-precipitation such as methanol is employed, to thereby precipitate the by-produced polymer and oligomer. The precipitates are removed through a technique such as filtration. Examples of a subsequent purification procedure include distillation, crystallization, and separation by means of a column. An appropriate purification procedure may be selected in accordance with properties of the reaction product and the type of impurities.

The thus-produced compounds may be identified through gas chromatography (GC), liquid chromatography (LC), gas chromatography-mass analysis (GC-MS), nuclear magnetic resonance spectrometry (NMR), infrared spectrometry (IR), melting point measurement, or a similar method.

The present invention also provides a method for producing the adamantane derivative represented by the following formula. Specifically, the adamantane derivative represented by the following formula (I-b) can be produced from an adamantane derivative represented by the following formula (III):

[F9]

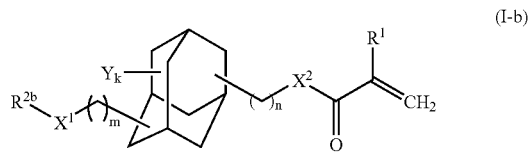

(I-b)

[F10]

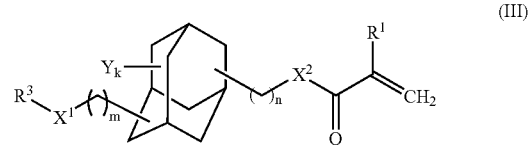

(III)

(wherein $R^1$, $X^1$, $X^2$, Y, k, m, and n have the same meanings as defined above, and $R^3X^1$ represents a leaving group) as a starting material. Examples of the leaving group denoted by $R^3$ in formula (III) include a methanesulfonyl group, a trifluoromethanesulfonyl group, and a p-toluenesulfonyl group.

Examples of the adamantane derivative represented by formula (III) include 3-methanesulfonyloxy-1-adamantyl acrylate, 3-methanesulfonyloxy-1-adamantyl methacrylate, 3-methanesulfonyloxy-1-adamantyl α-trifluoromethylacrylate, 3-trifluoromethanesulfonyloxy-1-adamantyl acrylate, 3-trifluoromethanesulfonyloxy-1-adamantyl methacrylate, 3-trifluoromethanesulfonyloxy-1-adamantyl α-trifluoromethylacrylate, 3-toluenesulfonyloxy-1-adamantyl acrylate, 3-toluenesulfonyloxy-1-adamantyl methacrylate, 3-toluenesulfonyloxy-1-adamantyl α-trifluoromethylacrylate, 3-nitrobenzenesulfonyloxy-1-adamantyl acrylate, 3-nitrobenzenesulfonyloxy-1-adamantyl methacrylate, 3-nitrobenzenesulfonyloxy-1-adamantyl α-trifluoromethylacrylate, 3-methanesulfonyloxy-1-adamantylmethyl acrylate, 3-methanesulfonyloxy-1-adamantylmethyl methacrylate, 3-methanesulfonyloxy-1-adamantylmethyl α-trifluoromethylacrylate, 3-trifluoromethanesulfonyloxy-1-adamantylmethyl acrylate, 3-trifluoromethanesulfonyloxy-1-adamantylmethyl methacrylate, 3-trifluoromethanesulfonyloxy-1-adamantylmethyl α-trifluoromethylacrylate, 3-toluenesulfonyloxy-1-adamantylmethyl acrylate, 3-toluenesulfonyloxy-1-adamantylmethyl methacrylate, 3-toluenesulfonyloxy-1-adamantylmethyl α-trifluoromethylacrylate, 3-nitrobenzenesulfonyloxy-1-adamantylmethyl acrylate, 3-nitrobenzenesulfonyloxy-1-adamantylmethyl methacrylate, 3-nitrobenzenesulfonyloxy-1-adamantylmethyl α-trifluoromethylacrylate, 3-methanesulfonyloxymethyl-1-adamantylmethyl acrylate, 3-methanesulfonyloxymethyl-1-adamantylmethyl methacrylate, 3-methanesulfonyloxymethyl-1-adamantylmethyl α-trifluoromethylacrylate, 3-trifluoromethanesulfonyloxymethyl-1-adamantylmethyl acrylate 3-trifluoromethanesulfonyloxymethyl-1-adamantylmethyl methacrylate, 3-trifluoromethanesulfonyloxymethyl-1-adamantylmethyl α-trifluoromethylacrylate, 3-toluenesulfonyloxymethyl-1-adamantylmethyl acrylate, 3-toluenesulfonyloxymethyl-1-adamantylmethyl methacrylate, 3-toluenesulfonyloxymethyl-1-adamantylmethyl α-trifluoromethylacrylate, 3-nitrobenzenesulfonyloxymethyl-1-adamantylmethyl acrylate, 3-nitrobenzenesulfonyloxymethyl-1-adamantylmethyl methacrylate, 3-nitrobenzenesulfonyloxymethyl-1-adamantylmethyl α-trifluoromethylacrylate, 3-methanesulfonylthio-1-adamantyl acrylate, 3-methanesulfonylthio-1-adamantyl methacrylate, 3-methanesulfonylthio-1-adamantyl α-trifluoromethylacrylate, 3-trifluoromethanesulfonylthio-1-adamantyl acrylate, 3-trifluoromethanesulfonylthio-1-adamantyl methacrylate, 3-trifluoromethanesulfonylthio-1-adamantyl α-trifluoromethylacrylate, 3-toluenesulfonylthio-1-adamantyl acrylate, 3-toluenesulfonylthio-1-adamantyl methacrylate, 3-toluenesulfonylthio-1-adamantyl α-trifluoromethylacrylate, 3-nitrobenzenesulfonylthio-1-adamantyl acrylate, 3-nitrobenzenesulfonylthio-1-adamantyl methacrylate, and 3-nitrobenzenesulfonylthio-1-adamantyl α-trifluoromethylacrylate. Of these, 3-methanesulfonyloxy-1-adamantyl acrylate and 3-methanesulfonyloxy-1-adamantyl methacrylate are preferred in the present invention.

The aforementioned adamantane derivative represented by formula (I-b) may be produced from an adamantane derivative represented by formula (III) as a starting material. In one specific procedure the starting adamantane derivative is reacted to a (thio)alcohol in the presence of a base, to thereby produce the formula (I-b) adamantane derivative.

Examples of the (thio)alcohol include methanol, ethanol, n-propanol, isopropanol, n-butanol, isobutanol, sec-butanol, tert-butanol, pentanol, hexanol, heptanol, octanol, nonanol, n-decanol, adamantanol, adamantylmethylthiol, 2-methyl-2-adamantanol, methanethiol, ethanethiol, n-propanethiol, isopropanethiol, n-butanethiol, isobutanethiol, sec-butanethiol, tert-butanethiol, pentanethiol, hexanethiol, heptanethiol, octanethiol, nonanethiol, n-decanethiol, adamantanethiol, 2-methyl-2-adamantanethiol, bis(mercaptotricyclo[5.2.1.0$^{2,6}$]decyloxy)ethylene, bis(mercaptotricyclo[5.2.1.0$^{2,6}$]decyl)ether, (mercaptotricyclo[5.2.1.0$^{2,6}$]decyloxy)propanethiol (mercaptopentacyclo[9.2.1.1$^{3,9}$.0$^{2.10}$.0$^{4,8}$]pentadecane)-propanethiol, (mercaptopentacyclo[9.2.1.1$^{4,7}$.0$^{2.10}$.0$^{3,8}$]pentadecane)-propanethiol, mercaptotricyclo[5.2.1.0$^{2,6}$]decylthiol, [mercaptomethyl(tricyclo[5.2.1.0$^{2,6}$]decyl)]methanethiol, mercaptopentacyclo[9.2.1.1$^{3,9}$.0$^{2.10}$.0$^{4,8}$]pentadecylthiol, mercaptopentacyclo[9.2.1.1$^{4,7}$.0$^{2.10}$.0$^{3,8}$]pentadecylthiol, 1,4-dithian-2,5-diol, 1,4-dithian-2,5-diyldimethanol, 5-hydroxymethyl-1,4-dithianyl-2-methanol, 5-mercaptomethyl-1,4-dithianyl-2-methanethiol, and 4-thiatricyclo[3.2.1.0$^{3,6}$]octan-2,8-diol. Of these, 1,4-dithian-2,5-diol and 1,4-dithian-2,5-diyldimethanol are preferred in the present invention.

The (thio)alcohol is generally fed in an amount of about 1 to about 100 mol based on 1 mol of the adamantane derivative represented by formula (III), preferably 20 to 40 mol.

Examples of the base include sodium amide, triethylamine, tributylamine, trioctylamine, pyridine, N,N-dimethylaniline, 1,5-diazabicyclo[4.3 0]nonene-5 (DBN), 1,8-diazabicyclo[5.4.0]undecene-7 (DBU), sodium hydroxide, potassium hydroxide, sodium hydride, potassium carbonate, silver oxide, sodium methoxide, and potassium t-butoxide. Of these, triethylamine and pyridine are preferred in the present invention.

The base is generally fed in an amount of about 0.1 to about 50 mol based on 1 mol of the adamantane derivative represented by formula (III), preferably 1 to 5 mol.

The solvent, reaction conditions, and other conditions employed are the same as employed in the synthesis from the adamantane derivative represented by formula (II) as a starting material.

Polymers of the modified alkyl (thio)ether-substituted adamantyl (meth)acrylate represented by formula (I-a) suitably serve as a photosensitive material for photoresists. The polymers may be produced through homopolymerization of the modified alkyl (thio)ether-substituted adamantyl (meth)acrylate or through copolymerization of the modified alkyl (thio)ether-substituted adamantyl (meth)acrylate with another co-monomer. In the case of copolymerization, the ratio by mass of modified alkyl (thio)ether-substituted adamantyl (meth)acrylate to another co-monomer is preferably 50/50 to 1/99, more preferably 25/75 to 5/95.

EXAMPLES

The present invention will next be described in more detail by way of examples, which should not be construed as limiting the invention thereto.

Example 1

Synthesis of 3-methylthiomethyloxy-1-adamantyl methacrylate

To a glass reactor (capacity: 1L) equipped with an agitator, 3-hydroxy-1-adamantyl methacrylate [Adamantate HM, product of Idemitsu Kosan Co., Ltd., FW (molecular weight): 236.31] (52.02 g, 220 mmol) and methoquinone (52 mg, 1,000 ppm by mass) serving as an inhibitor were added.

DMSO (dimethylsulfoxide) [FW: 78.14, d (density 1.101 g/cm$^3$] (450 mL, 6.3 mol) and acetic anhydride [FW: 102.09, d: 1.082 g/cm$^3$] (300 mL, 3.2 mol) were added to the adamantane derivative. Through stirring, the mixture was gradually dissolved, and the solution was allowed to react at room temperature. After 48 hours from the start of reaction, percent conversion of the starting materials of about 100% was confirmed through GC (gas chromatography).

The reaction mixture was transferred to a separating funnel, and diethyl ether (500 mL) and water (200 mL, were added to the mixture, followed by vigorous shaking. The mixture was left to stand, and the lower aqueous layer was separated from the mixture. The procedure was further repeated five times.

Subsequently, 10-mass % aqueous ammonia (100 mL) was added to the organic layer, followed by vigorous shaking. The mixture was left to stand, whereby the lower aqueous layer was separated from the mixture. The procedure was further repeated twice. The final aqueous layer was confirmed to have a pH of about 6.

The organic layer was dried with sodium sulfate anhydrate, and the solvent was removed. Further, light impurities were removed through distillation under reduced pressure (50° C./≦0.1 kPa). The distillation residue was added slowly and dropwise to methanol (300 mL) while it was vigorously stirred, whereby the formed polymers and oligomers were re-precipitated. The precipitates were filtered out by means of a membrane filter (pore size: 0.5 μm).

Methanol was thoroughly removed from the thus-produced solution, and the residue was dissolved in hexane (200 mL). The solution was decolored by adding activated carbon (5 g) to the solution, and the decolored solution was filtered through a membrane filter (pore size: 0.5 μm) Subsequently, hexane was removed and dried under reduced pressure, to thereby yield 47.09 g of a target 3-methylthiomethyloxy-1-adamantyl methacrylate (FW: 269.43, isolated yield: 72.2%). The product was found to have a GC purity of 99% or higher and a GPC purity of 99%.

The thus-produced compound was analyzed through nuclear magnetic resonance spectrometry (NMR) and gas chromatography-mass analysis (GC-MS). The thus-determined physical properties are as follows.

Physical Properties

Nuclear magnetic resonance spectrometry (NMR): $CDCl_3$ $^1$H—NMR (500 MHz): 1.56 (dd, J=13.0 Hz, 32.9 Hz, 2H, h or i), 1.80 (dd, J=11.1 Hz, 37.9 Hz, 4H, f or j), 1.89 (s, 3H, a), 2.09 (dd, J=11.5 Hz, 40.5 Hz, 4H, j or f), 2.19 (s, 3H, m), 2.23 (s, 2H, g), 2.36 (br-s, 2H, i or h), 4.60 (s, 2H, l), 5.49 (t, J=1.5 Hz, 1H, b$^1$), 6.01 (s, 1H, b$^2$) $^{13}$C—NMR $^{127}$ MHz): 14.29 (m), 18.23(a), 30.90 (h), 34.93 (g or i), 40.01 (f or j), 40.45 (j or f), 45.33 (i or g), 65.95 (l), 75.72 (k), 81.10 (e), 124.58 (b), 137.63 (c), 166.25 (d)

[F11]

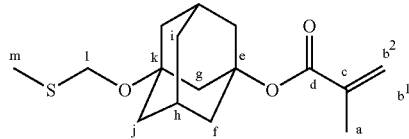

Gas chromatography-mass analysis (GC-MS): EI 297 (M$^+$+1, 0.3%), 296 (M$^+$, 1.7%), 266 (4.3%) 249 (5.7%), 219 (55.7%), 133 (16.8%), 69 (100%), 61 (16.7%)

The thus-produced compound was measured in terms of refractive index and Abbe's number. Table 1 shows the results.

Determination of Refractive Index and Abbe's Number

Refractive index of a compound which assumes liquid at 23° C. was measured at 23° C. by means of an Abbe's refractometer (product of Atago Co., Ltd.). In the case of a compound which is solid at 23° C., the compound was dissolved in tetrahydrofuran, and refractive index of the solution was measured at 23° C. Abbe's number was calculated from the refractive index. Specifically, refractive index of 3-methylthiomethyloxy-1-adamantyl methacrylate was measured in the liquid states whereas refractive indexes of 1-adamantyl methacrylate and 3-hydroxy-1-adamantyl methacrylate were measured in the form of tetrahydrofuran solutions.

Comparative Examples 1 and 2

In a manner similar to that of Example 1, refractive indexes and Abbe' numbers of 1-adamantyl methacrylate (Comparative Example 1) and 3-hydroxy-1-adamantyl methacrylate (Adamantate HM, product of Idemitsu Kosan Co., Ltd.) (Comparative Example 2) were measured. The results are shown in Table 1.

Table 1

TABLE 1

| Samples | | Refractive index $n_D$ | Abbe's No. |
|---|---|---|---|
| Ex. 1 | 3-methylthiomethyloxy-1-adamantyl methacrylate | 1.5226 | 46.2 |
| Comp. Ex. 1 | 1-adamantyl methacrylate | 1.4987 | 48.0 |
| Comp. Ex. 2 | 3-hydroxy-1-adamantyl methacrylate (Adamantate HM, product of Idemitsu Kosan Co., Ltd.) | 1.5099 | 54.4 |

INDUSTRIAL APPLICABILITY

The novel modified alkyl (thio)ether-substituted adamantyl (meth)acrylate of the present invention is useful as a monomer for producing functional resins such as photosensitive resins particularly for use in lithography, and is preferably employed in the field where specific optical properties (i.e., refractive index and Abbe's number) are required.

The invention claimed is:

1. An adamantane derivative having a structure represented by formula (I-a):

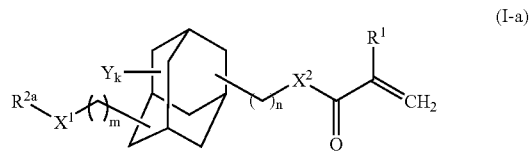

wherein:
R$^1$ represents a hydrogen atom, a methyl group, or a trifluoromethyl group;
R$^{2a}$ represents a C1 to C30 alkyl group or a hydrocarbon group containing a C3 to C30 cycloalkyl group or a C6 to C30 aryl group, the alkyl group or the hydrocarbon group having a sulfide group;
each of X$^1$ and X$^2$ represents an oxygen atom or a sulfur atom;
Y represents a C1 to C10 alkyl group, a halogen atom, a hydroxyl group, or a mercapto group, or two Ys are linked to form =O or =S;
a plurality of Ys may be identical to or different from one another; k represents an integer of 0 to 14; and
each of m and n is an integer of 0 to 2.

2. A method for producing an adamantane derivative having a structure represented by formula (I-a):

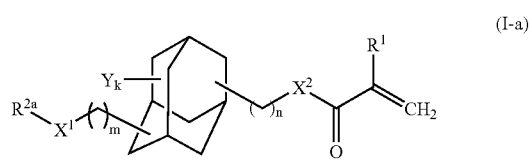

wherein:
R$^1$ represents a hydrogen atom, a methyl group, or a trifluoromethyl group;
R$^{2a}$ represents a C1 to C30 alkyl group or a hydrocarbon group containing a C3 to C30 cycloalkyl group or a C6 to C30 aryl group, the alkyl group or the hydrocarbon group having a sulfur atom;

each of $X^1$ and $X^2$ represents an oxygen atom or a sulfur atom;

Y represents a C1 to C10 alkyl group, a halogen atom, a hydroxyl group, or a mercapto group, or two Ys are linked to form =O or =S;

a plurality of Ys may be identical to or different from one another; k represents an integer of 0 to 14; and each of m and n is an integer of 0 to 2; and wherein the method comprises reacting an adamantane derivative represented by formula (II) with a sulfoxide in an acid anhydride:

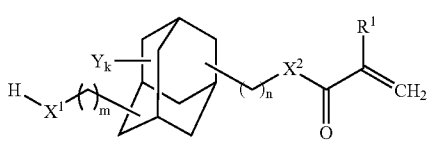

(II)

wherein $R^1$, $X^1$, $X^2$, Y, k, m, and n have the same meanings as defined above.

3. A method as described in claim 2, wherein the adamantane derivative represented by formula (II) is 3-hydroxy-1-adamantyl (meth)acrylate.

4. A method for producing an adamantane derivative having a structure represented by formula (I-b):

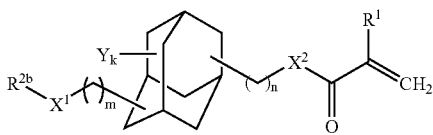

(I-b)

wherein:
- $R^1$ represents a hydrogen atom, a methyl group, or a trifluoromethyl group;
- $R^{2b}$ represents a $C^1$ to C30 alkyl group or a hydrocarbon group containing a C3 to C30 cycloalkyl group or a C6 to C30 aryl group, and $R^{2b}$ may have a sulfur atom;
- each of $X^1$ and $X^2$ represents an oxygen atom or a sulfur atom;
- Y represents a C1 to C10 alkyl group, a halogen atom, a hydroxyl group, or a mercapto group, or two Ys are linked to form =O or =S;
- a plurality of Ys may be identical to or different from one another;
- k represents an integer of 0 to 14; and
- each of m and n is an integer of 0 to 2;

wherein the method comprises reacting an adamantane derivative represented by formula (III) with a thioalcohol in the presence of a base:

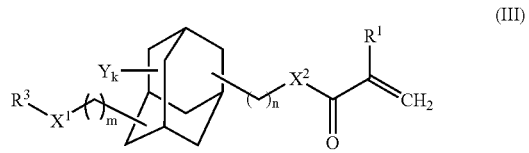

(III)

wherein $R^1$, $X^1$, $X^2$, Y, k, m, and n have the same meanings as defined above, and $R^3X^1$ represents a leaving group.

5. A method as described in claim 4, wherein the adamantane derivative represented by formula (III) is 3-methanesulfonyloxy-1-adamantyl (meth)acrylate.

6. A photosensitive material for photoresist, which material comprises a polymer formed from, as a component thereof, an adamantane derivative represented by formula (I-a):

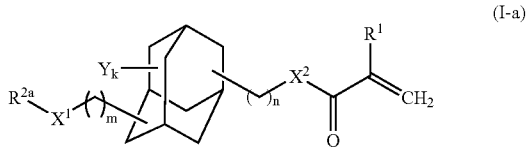

(I-a)

wherein:
- $R^1$ represents a hydrogen atom, a methyl group, or a trifluoromethyl group;
- $R^{2a}$ represents a C1 to C30 alkyl group or a hydrocarbon group containing a C3 to C30 cycloalkyl group or a C6 to C30 aryl group, the alkyl group or the hydrocarbon group having a sulfur atom;
- each of $X^1$ and $X^2$ represents an oxygen atom or a sulfur atom;
- Y represents a C1 to C10 alkyl group, a halogen atom, a hydroxyl group, or a mercapto group, or two Ys are linked to form =O or =S;
- a plurality of Ys may be identical to or different from one another;
- k represents an integer of 0 to 14; and
- each of m and n is an integer of 0 to 2.

* * * * *